United States Patent [19]
Egley et al.

[11] Patent Number: 5,963,615
[45] Date of Patent: Oct. 5, 1999

[54] ROTATIONAL FLATNESS IMPROVEMENT

[75] Inventors: Bert David Egley; Joseph Scott Saba, both of Walnut Creek, Calif.

[73] Assignee: Siemens Medical Systems, Inc., Iselin, N.J.

[21] Appl. No.: 08/907,582

[22] Filed: Aug. 8, 1997

[51] Int. Cl.⁶ .................................................. A61N 5/10
[52] U.S. Cl. ................................... 378/65; 250/492.3
[58] Field of Search ............................ 378/65; 250/492.3

[56] References Cited

U.S. PATENT DOCUMENTS

| | | | |
|---|---|---|---|
| 3,955,089 | 5/1976 | McIntyre et al. | 378/65 |
| 5,189,687 | 2/1993 | Bova et al. | 378/65 |

*Primary Examiner*—Craig E. Church

[57] ABSTRACT

A radiation treatment apparatus (10) including a stand (12), a gantry (14) movably supported on the stand (12), the gantry (14) having a vertical section (16) and a generally linear cantilevered strut section (18), the cantilevered strut section (18) having a supported end adjacent the vertical section (16) and a projecting end opposite the supported end, a substantially linear particle accelerator (30) disposed within and longitudinally supported in generally parallel relationship with the cantilevered strut section (18), the accelerator (30) having a predetermined injection point (32) where particles are launched in the accelerator and a predetermined exit point (34) where the particles are discharged from the accelerator, a treatment head (22) coupled to the remote end of the cantilevered strut section proximate the exit point (34), the treatment head (22) for emitting a radiation beam (27), and a tuneable stiffening apparatus (40) attached to the accelerator (30) for substantially maintaining alignment between accelerated particle beam (27) and the bending magnet (35) and target (39) supported by the strut section (18).

12 Claims, 4 Drawing Sheets

ROTATIONAL FLATNESS IMPROVEMENT

BACKGROUND OF THE INVENTION

The invention relates generally to a radiation treatment apparatus, and more particularly to such apparatus employing a linear accelerator to provide X-rays or other particle beams for therapeutic medical applications. Such linear accelerators typically have an injection point where particles originate in the accelerator, an insertion point where RF energy enters the accelerator, and an exit point from which the particles are discharged from the accelerator. The particles may be used directly for treatment or converted to X-rays by striking a target, typically made from a high density material such as gold.

The use of linear accelerators in radiation therapy is generally known. Linear accelerators are used for generating a high energy radiation beam to be directed at tissue for treatment. As is well-known, a typical radiation therapy apparatus includes a stand anchored firmly to the floor of a room and a gantry rotatable on a bearing in the stand. The operational accelerator structure, housed within and oriented substantially parallel to a cantilevered strut section of the gantry, is rotatable with the gantry about the bearing to enable the treatment head at the remote end of the strut section to be positioned in a continuum of positions and orientations around a patient or object situated on a platform at the isocenter of the apparatus.

While such radiation therapy systems have been very successful, a problem has arisen in radiation therapy systems employing cantilevered linear accelerators. When the gantry is oriented at specific angular positions/orientations with respect to the stand, the accelerated particle beam may become slightly misdirected with respect to the target, producing potentially unsatisfactory results. More particularly, depending upon the angular position of the gantry, the cantilevered strut section of the gantry and the similarly cantilevered linear accelerator disposed therein differentially deflect. This differential deflection will cause the particle beam to follow a different path within the bending magnet and to strike the target at different input angles, ultimately affecting the X-ray beam intensity profile of the radiated X-rays as the gantry is rotated. The flatness of the beam intensity profile at all gantry angles is referred to as "rotational flatness".

Attempts have been made to electronically correct the misalignment problem attributable to gravitational deflection, but such efforts, standing alone, have not been entirely effective. In particular, such electronic solutions must generally include circuitry to measure the amount of misalignment and incorporate a feedback mechanism to correct for the misalignment. An example of an appropriate feedback mechanism is one or more wound coils disposed proximately to the beam path for directing the beam path. This type of solution is considerably more complex than the invention disclosed herein, and fails to likewise address the cause of the misalignment problem.

Additional attempts have been made to improve rotational flatness by stiffening the support plate used to affix the linear waveguide accelerator to the cantilevered gantry section. However, such methods for resolving the rotational flatness problem have been relatively ineffective because they offer no ready means of adjustment.

SUMMARY OF THE INVENTION

In accordance with the present invention there is provided a radiation treatment apparatus with an improved rotational flatness characteristic. In particular, the inventive radiation treatment apparatus improves the rotational flatness characteristic of the radiation treatment apparatus by mechanically matching the deflection of the accelerated particle beam and the bending magnet supported by the cantilevered strut in which the accelerator is housed.

The radiation treatment apparatus includes a stand for movably supporting a gantry thereon; the gantry having a vertical section and a generally linear cantilevered strut section. Inside the cantilevered strut section of the gantry, and longitudinally supported in generally parallel relationship therewith, is a substantially linear particle accelerator. In order to improve the rotational flatness characteristic of the radiation treatment apparatus, a tuneable stiffening apparatus or other means for maintaining alignment between the accelerated particle beam and the bending magnet housed in the cantilevered strut section is provided. By maintaining beam alignment, the rotational flatness is greatly improved.

BRIEF DESCRIPTION THE DRAWINGS

DETAILED DESCRIPTION OF THE PREFERRED EMBODIMENT

Figure 1:
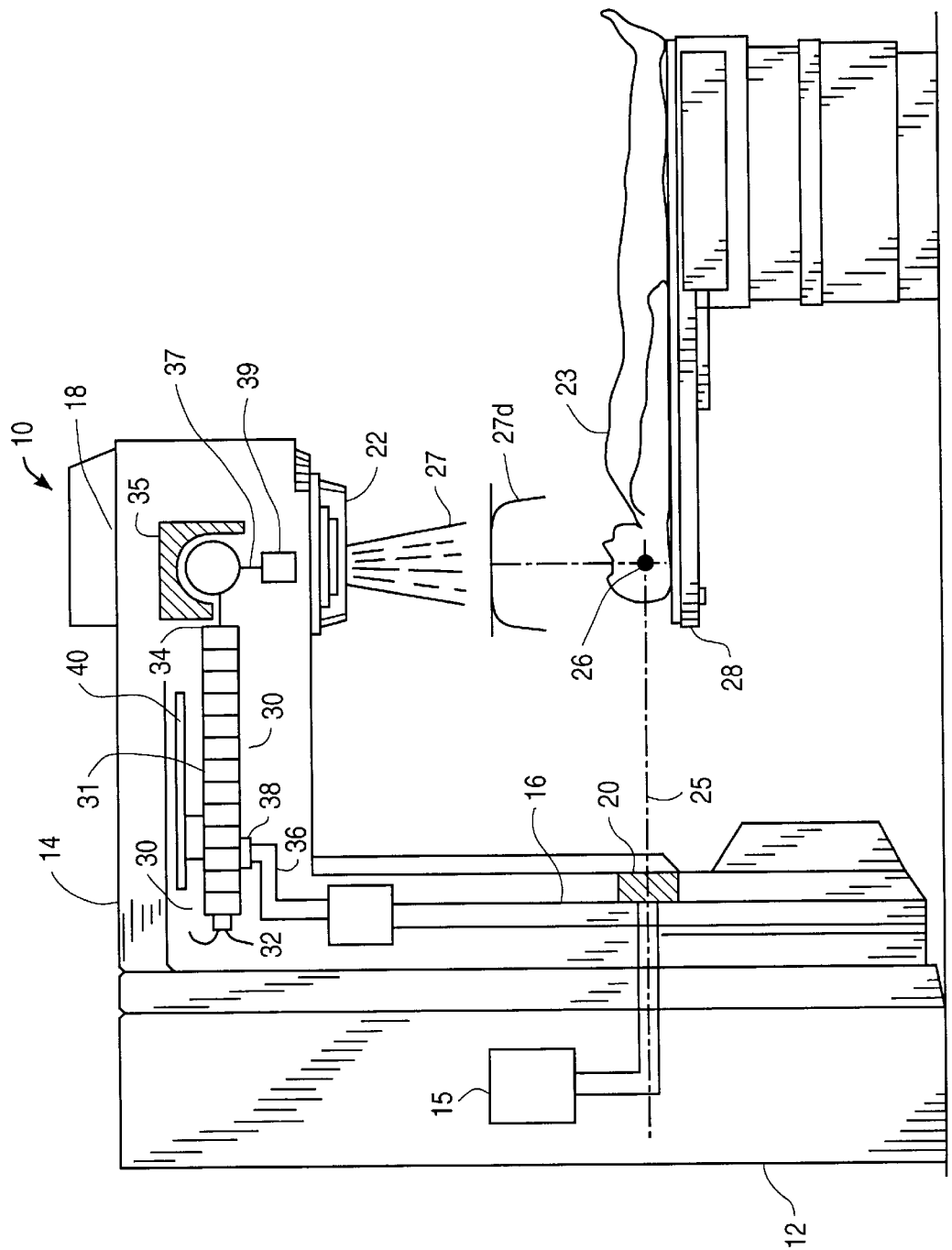
FIG. 1 is an elevation view of radiation treatment apparatus according to the present invention showing specific internal components thereof.

Referring to the drawings and especially to FIG. 1, a radiation treatment apparatus 10 is shown such that specific internal components of the apparatus are visible. The radiation treatment apparatus 10 includes a stand 12 and a gantry 14 rotatable on a bearing 20 which transversely extends through the stand 12 and gantry 14. The gantry 14 may be formed in two sections: a vertical section 16, and a cantilevered strut section 18; the cantilevered strut section 18 being generally perpendicular to and cantilevered from the vertical section 16. At the end of the strut section 18, remote from the vertical section 16, is a treatment head 22 from which a radiation beam 27 generated by the apparatus is directed toward a patient 23 situated on platform 28.

A linear accelerator 30 is disposed within and longitudinally supported in generally parallel relationship with the cantilevered strut section 18. The accelerator 30 has a linear accelerating portion 31 and an RF insertion waveguide portion 36 extending substantially perpendicularly from the linear accelerating portion 31 at a junction 38. At the end of the accelerator 30, remote from the treatment head 22, is a particle gun 32, or "injection point", of the accelerator. The particles exit the linear portion of the accelerator 30 at point 34, where they enter a 270° achromatic bending magnet 35 and exit at point 37 to strike a high density target 39 from which X-rays 27 are created. The RF insertion waveguide portion 36 provides transmission of RF energy, thereby enabling particle acceleration within the accelerator 30. The RF energy is typically provided by a magnetron or klystron 15. The RF energy enters the linear accelerating portion 31 of the accelerator 30 at the accelerator junction 38.

Figure 1A:
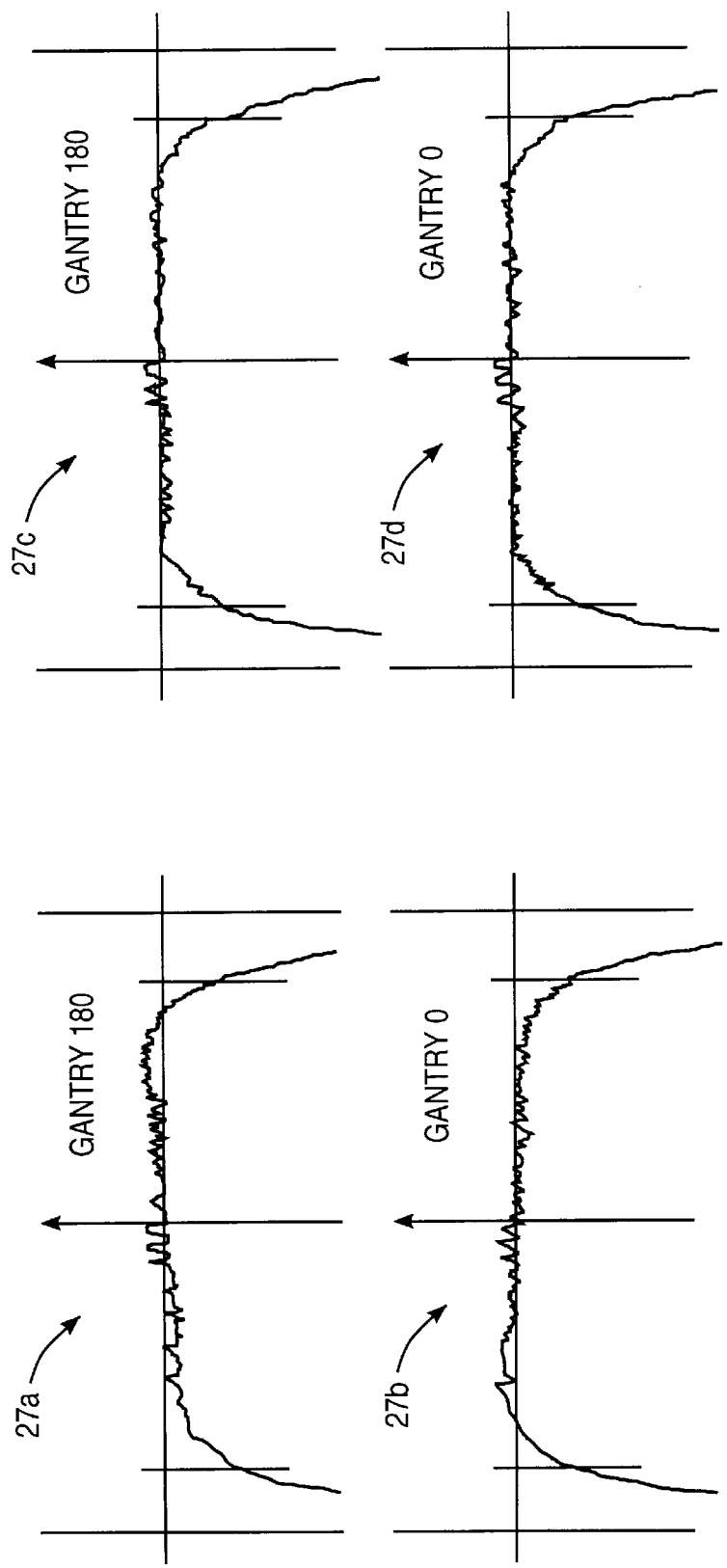
FIG. 1a is a diagram illustrating exemplary beam intensity profile graphs.

In operation, the generated X-rays 27 are used to treat a treatment area, such as a cancer tumor 26 at or near the isocenter. Notably, the X-ray energy delivered to the treatment area 26 is constant regardless of the angular position of the gantry. A normalized beam intensity profile with the gantry up, or at zero degrees, is shown in FIG. 1a at graph 27b, and one with the gantry down, or at 180 degrees, is shown in FIG. 1a at graph 27a. These are typical of sub-optimal rotational flatness. The beam intensity profile graph 27a has a positive slope and energy profile graph 27b has a negative slope; neither is flat. Examples of energy profiles which are flat at all gantry angles are shown in FIG. 1a at graphs 27c and 27d, and in FIG. 1 at 27d.

In order to facilitate applying a radiation beam to a properly situated patient from one of a continuum of angular positions, the gantry 14 may be rotated on its bearing 20 about a rotational axis 25 with respect to the stand 12 so that the treatment head 22 encircles the patient located at the isocenter 26 of the apparatus. Thus, the cantilevered strut section 18 may be positioned with respect to stand 12 in a continuum of positions angularly identified from 0° to 360°.

The angular orientation of the gantry 14 contributes to the application of deflection forces on the bending magnet 35 and the accelerator 30 therein. Additional bending and torsional forces are also present due to the weight of the treatment head 22 and its position at the end of the strut section 18. The bending magnet 35 and accelerator thus have differential deflections at different angular orientations of the gantry 14 (i.e., the accelerator 30 and the bending magnet 35 deflect at different angles). These differential deflections can result in a relative misalignment between the components such that the accelerated particle beam hits the target 39 at different input angles depending upon the angular orientation of the gantry 14, affecting the flatness of the X-ray beam intensity profile shown in FIG. 1a at graphs 27a and 27b.

One approach to solving this problem would be to couple the accelerator 30 and the bending magnet 35 together nearer the treatment head 22. However, the density of components near the treatment head 22 makes this approach unfeasible. Additionally, directly coupling the accelerator to the bending magnet at one point only constrains position (translation), not slope (rotation), at that point. Accordingly, in order to resolve these problems, a tuneable plate 40 according to the present invention is used to affix the accelerator 30 to strut section 18. The stiffness of the plate 40 is chosen, as will be discussed in greater detail below, such that the particle beam remains aligned with the bending magnet 35, thereby improving the rotational flatness characteristic of the machine.

Figure 2:
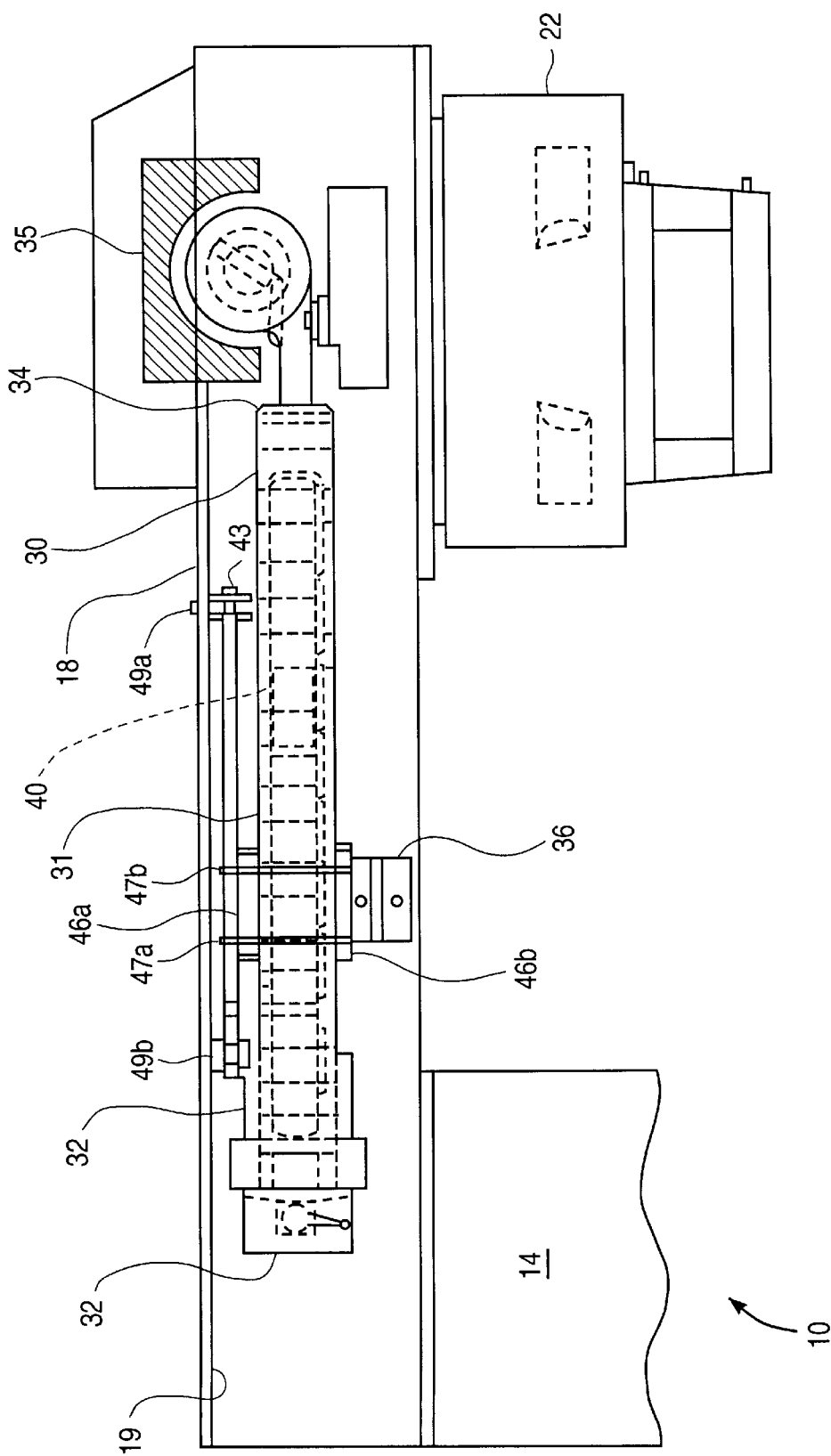
FIG. 2 is an enlarged elevation view of a cantilevered strut section and treatment head of a radiation treatment apparatus in accordance with the invention.

Referring now to FIG. 2, an embodiment of the invention which provides improved rotational flatness employs an improved support plate 40 to be attached to accelerator 30 to inhibit the above-described differential deflection. Specifically, the support plate 40 is coupled to the accelerator 30 by a pair of stabilizing blocks 46a and 46b. The blocks 46a and 46b and the support plate 40 may be held together by a number of long bolts 47a, 47b or other conventional means, while the accelerator 30 is firmly gripped between the blocks 46a and 46b. The support plate 40 is also attached to an inner surface 19 of the cantilevered strut section 18 by conventional means, such as machine screws or bolts 49a, 49b, which extend through the cantilevered strut section 18.

Figure 3:
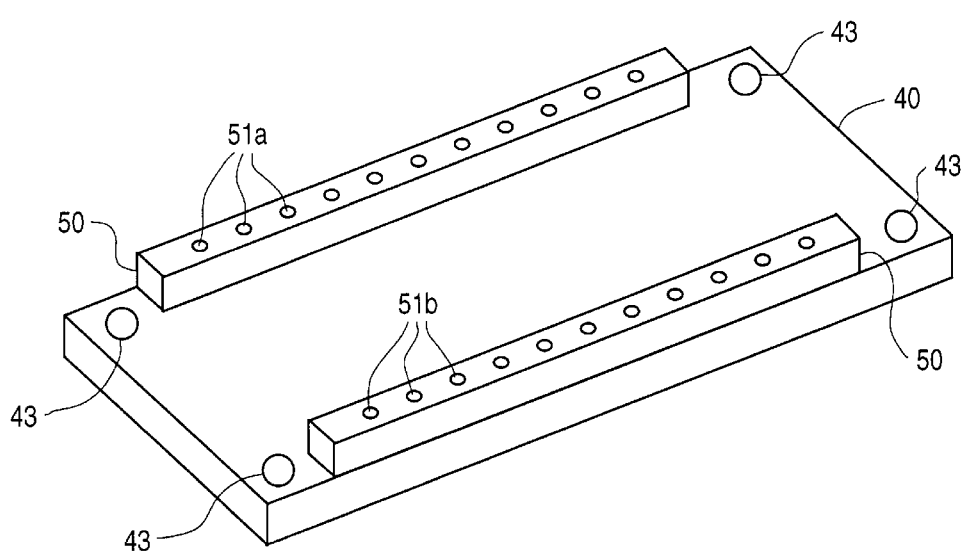
FIG. 3 is a perspective view of a stiffening apparatus in accordance with the invention.

The thickness of the support plate 40 is chosen to allow the deflection of the accelerator to be tuned to match the deflection of the bending magnet. Because different size accelerators deflect differently, a common support plate 40 is chosen, as seen in FIG. 3, and, in one embodiment, is provided with a pair of symmetrically placed stiffener bars 50 along opposite sides of the support plate 40. It is noted that, while illustrated as being generally rectangular, the support plate 40 may be of any suitable configuration. In addition, while two stiffener bars 50 are illustrated, one or more may be employed. Similarly, while a support plate 40 is shown, the support may be embodied in support bars having a predetermined stiffness disposed on opposite sides and/or above the accelerator assembly; additional stiffener bars configured for tuning the support bars may be provided. Thus, FIG. 3 is exemplary only.

As illustrated, the stiffener bars 50 preferably each have a plurality of holes 51a and 51b, which are used as bolt holes to affix the stiffener bars 50 to the plate 40. The plurality of holes allows use of a plurality of bolts, which allows "tuning" of the stiffness of the plate 40. In this manner a composite stiffness is achieved, wherein the radiation or accelerated particle beam remains aligned with the bending magnet and target. It is noted that while the stiffener bars 50 are illustrated with a plurality of holes, they may alternatively be configured to be affixed to the support plate 40 in any tuneable fashion, such as by clamps or welding, so long as the composite structure has a tuneable stiffness. Providing a plate having a tuneable stiffness thus permits the same plate and bars to be used for accelerators having different lengths. The plate 40 also has holes 43 for machine screws or bolts to be inserted therethrough for attachment to the cantilevered strut section 18.

The inclusion of the tuneable support plate 40 allows adjustment of the aggregate bending moment of inertia of the accelerator support assembly, thereby increasing or decreasing its deflection due to gravitation over its length. The support plate 40 is essentially a stiffening apparatus attached to the accelerator 30 for substantially maintaining alignment between the accelerated particle beam, bending magnet and target. Therefore, the tuneable rigidity provided by the plate 40 serves to improve the rotational flatness characteristic of the radiation treatment apparatus.

From the foregoing, it will be appreciated that the invention provides a novel radiation treatment apparatus and a method for maintaining relative alignment between the accelerated particle beam, bending magnet, and target to improve the rotational flatness of the device. The invention is not limited to the embodiment described herein, or to any particular embodiment. Specific examples of alternative embodiments considered to be within the scope of the invention include embodiments where the stiffening apparatus is attached to the accelerator or interior surface of the cantilevered strut section in a different manner than is described herein. Also, the invention contemplates a stiffening apparatus of differing configuration or material from that described in the preferred embodiment. Additionally, the invention contemplates a gantry which is differently movable or differently orientable with respect to the stand of the radiation treatment apparatus. Other modifications to the preferred embodiment may also be made within the scope of the invention. The invention is defined by the following claims.

What is claimed is:

1. A radiation treatment apparatus comprising:
   a gantry having a vertical section and a generally linear cantilevered strut section;
   a linear particle accelerator disposed within and longitudinally supported in generally parallel relationship with said cantilevered strut section for generating a radiation beam; and
   a tuneable stiffening apparatus attached to said accelerator and said strut section for enabling adjustment of the stiffness therebetween.

2. A radiation treatment apparatus in accordance with claim 1, wherein said tuneable stiffening apparatus comprises a mounting plate.

3. A radiation treatment apparatus in accordance with claim 2, wherein said tuneable stiffening apparatus further comprises at least one stiffener bar attached to said mounting plate, said stiffener bar providing said mounting plate with additional bending stiffness.

4. A radiation treatment apparatus in accordance with claim 3, wherein said stiffener bar is configured to be selectably attached to said mounting plate such that a composite stiffness of said stiffener bar and said mounting plate are selectably tuneable.

5. A radiation treatment apparatus in accordance with claim 4, wherein said stiffener bar includes a plurality of bolt holes adapted to receive a plurality of bolts for affixing said stiffener bar to said mounting plate.

6. A radiation treatment apparatus in accordance with claim 5, wherein said stiffening apparatus is also attached to said strut section thereby providing alignment between an accelerated particle beam generated by said particle accelerator, a bending magnet disposed at an end of said accelerator, and a target.

7. A radiation treatment apparatus comprising:
a stand;
a gantry movably supported on said stand, said gantry having a vertical section and a generally linear cantilevered strut section;
a particle accelerator for generating a radiation beam, said particle accelerator disposed within and longitudinally supported in generally parallel relationship with said cantilevered strut section; and
means for attaching said accelerator to said strut section, said attaching means including means for enabling the stiffness between said strut section and said accelerator to be varied.

8. A radiation treatment apparatus in accordance with claim 7, wherein said enabling means comprises a mounting plate.

9. A radiation treatment apparatus in accordance with claim 8, wherein said enabling means further comprises at least one stiffener bar attached to said mounting plate, said stiffener bar providing said mounting plate with additional bending stiffness.

10. A radiation treatment apparatus in accordance with claim 9, wherein said stiffener bar is configured to be selectably attached to said mounting plate such that a composite stiffness of said stiffener bar and said mounting plate are selectably tuneable.

11. A method for improving the rotational flatness in a radiation treatment apparatus having a stand, a gantry movably supported on said stand, said gantry having a vertical section and a cantilevered strut section, and a substantially linear particle accelerator for generating a radiation beam disposed within said cantilevered strut section, comprising:

(a) providing a tuneable stiffening apparatus;

(b) attaching said tuneable stiffening apparatus to said accelerator;

(c) attaching said stiffening apparatus to said cantilevered strut section; and (d) tuning said stiffening apparatus to vary the stiffness between said strut section and said accelerator.

12. A method according to claim 11, wherein said tuning includes maintaining the alignment of said radiation beam and a target supported in said strut section.

* * * * *